(12) United States Patent
Igaki et al.

(10) Patent No.: US 6,409,746 B1
(45) Date of Patent: Jun. 25, 2002

(54) EYE PILLOW

(75) Inventors: Michihito Igaki; Takeshi Oka; Tadayuki Tokunaga; Shinichi Sato, all of Tokyo (JP)

(73) Assignee: Kao Corporation, Tokyo (JP)

( * ) Notice: Subject to any disclaimer, the term of this patent is extended or adjusted under 35 U.S.C. 154(b) by 95 days.

(21) Appl. No.: 09/679,542

(22) Filed: Oct. 6, 2000

(30) Foreign Application Priority Data

Oct. 7, 1999 (JP) ............................................. 11-287435
Dec. 27, 1999 (JP) ............................................ 11-371966
Sep. 5, 2000 (JP) ......................................... 2000-269305

(51) Int. Cl.[7] .................................................... A61F 7/00
(52) U.S. Cl. .......................... 607/109; 607/114; 126/263
(58) Field of Search ................................ 607/109, 114; 126/263

(56) References Cited

U.S. PATENT DOCUMENTS

| | | | | |
|---|---|---|---|---|
| 5,046,479 A | * | 9/1991 | Usui | ........................ 126/204 |
| 5,233,981 A | | 8/1993 | Miyashita | |
| 5,643,336 A | * | 7/1997 | Lopez-Claros | ............... 607/104 |
| 5,720,773 A | * | 2/1998 | Lopez-Claros | ................ 607/96 |
| 6,090,060 A | * | 7/2000 | Radow | ......................... 602/74 |

FOREIGN PATENT DOCUMENTS

| | | |
|---|---|---|
| DE | 297 10 493 | 10/1997 |
| DE | 298 04 424 | 7/1998 |
| WO | WO 99/51174 | 10/1999 |

* cited by examiner

Primary Examiner—Michael Powell Buiz
Assistant Examiner—Meredith H Schoenfeld
(74) Attorney, Agent, or Firm—Oblon, Spivak, McClelland, Maier & Neustadt, P.C.

(57) ABSTRACT

The eye pillow of the present invention has a steam-generating unit that uses chemical energy. The temperature of steam released from the surface of the eye pillow which is applied to the eyes and the area around the eyes is kept at 50° C. or lower and total weight of the eye pillow is 50 g or more. Preferably, the eye pillow has the steam-generating unit and a cooler which are attached to the eye pillow body removably. Thus, the moisture as with a steamed towel and the cold as with a cold towel can be continuously introduced to the eyes and the area around the eyes easily and safely to relieve the dry eyes, etc., while applying an appropriate pressure to the eyes and the area around the eyes.

7 Claims, 5 Drawing Sheets x-x Cross Section x-x Cross Section x-x Cross Section x-x Cross Section x-x Cross Section x-x Cross Section

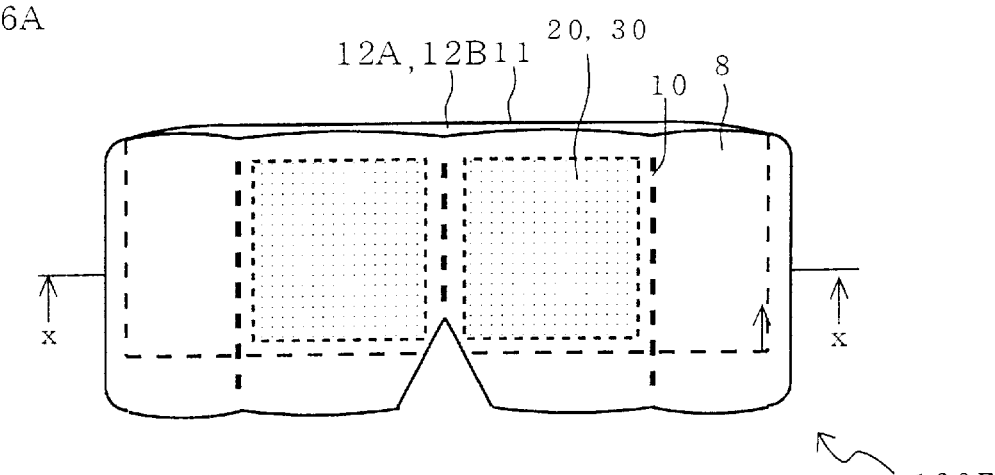
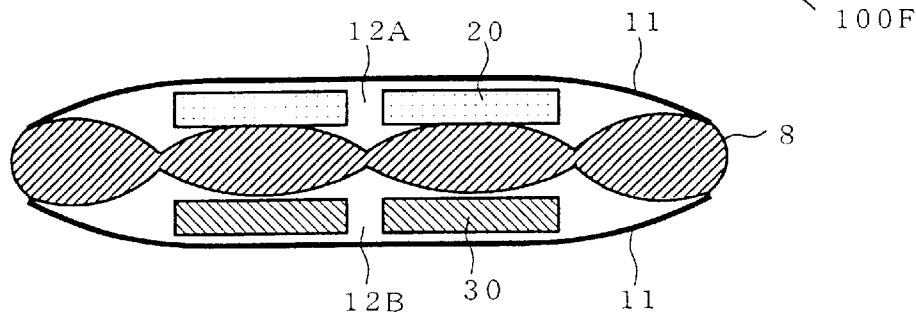
Fig. 6A
Fig. 6B
x-x Cross Section

EYE PILLOW

BACKGROUND OF THE INVENTION

1. Field of the Invention

The present invention relates to an eye pillow with which the eyes and the area around the eyes are cooled at a temperature that is not damaging or irritating or warmed at a steam temperature that is not damaging or irritating in order to alleviate and improve eyestrain, the main cause of which is dry, burning eyes, and thereby provide comfort by relaxing, refreshing, etc., and induce a pleasant sleep.

2. Description of the Related Art

Many people complain of eye fatigue (eyestrain) in today's stressful world flooded with information. Dry eyes as a result of operating a VDT (visual display terminal), such as a computer terminal, driving an automobile, watching television or videos, playing video games, studying, reading, etc., are one of the main causes of eyestrain. As a result of the eyes staring and blinking very few times while operating a VDT, etc., the eyes become bloodshot, the accommodation muscles around the eyes become over-strained, and there is an increase in the amount of evaporation of tears, which are an important protective component of the surface of the eyes, and the eyes thereby become dry. The environment in which a VDT is operated today is generally air-conditioned and in a state of low moisture and therefore, the eyes easily become dry. This probably exacerbates eyestrain due to dry eyes.

Furthermore, many people now wear contact lenses that float in tears on the cornea. Therefore, there is a possibility that the cornea will be scratched by a contact lens when the eyes become dry, particularly in persons who secrete few tears. Dry-eyes causes not only eyestrain, but also the other problems.

Moreover, mental stress accumulates with long-term OA operation, etc., and causes an unstable mental state and insomnia, etc.

Eye drops, application of cold towels or steam towels to the eyes, etc., are used to treat eyestrain. Moreover, eye pillows are also being used to apply the appropriate weight to the eyes and the area around the eyes and provide relaxation and induce sleep.

Eye drops are effective against dry eyes, but the preservatives that are added to eye drops for shelf life can actually cause new damage.

On the other hand, it is possible to provide the eyes with cool or warm moisture that is safe using a cold towel or a steam towel, but they cannot be easily used and they cannot necessarily be used anywhere and at anytime.

Methods that use chemical energy, such as the heat of neutralization of acids and alkalis, the heat of hydration of inorganic salts, the heat of oxidation of metals, such as iron powder, etc., to heat water to generate steam are methods of applying steam to the eyes. However, even though steam is easily generated by these methods, it is difficult to control the temperature of the steam and there is a problem with direct application in terms of safety.

Cold packs that use a water-containing agent and a heat-absorbing agent that reacts with water to induce an endothermic reaction are known as a method of cooling the eyes. Nevertheless, the main purpose of product development of cold packs was either how to bring the temperature of the pack itself to a low temperature or how to prolong the cold insulation time and they cannot effectively alleviate eyestrain or stress when applied to the eyes for a short period of time.

Moreover, even though the purpose of the eye pillow is to alleviate stress and insomnia, this effect is actually only felt by some people.

SUMMARY OF THE INVENTION

The object of the present invention is to easily and continuously apply the moisture in a safe way as with a steam towel or a cold towel to the eyes and the area around the eyes while applying an appropriate pressure to the eyes and the area around the eyes in order to prevent stress, insomnia, etc., due to dry, burning eyes and overuse of eyes, which cause eyestrain and other problems.

In order to accomplish the above-mentioned object, the present invention provides an eye pillow applied to the eyes and the area around the eyes whose total weight is 50 g or more, comprising a steam-generating unit that uses chemical energy and wherein steam at 50° C. or lower is released from the surface of the eye pillow that is applied to the eyes and the area around the eyes.

It particularly provides an embodiment wherein the steam-generating unit can be attached to or detached from the eye pillow body as needed and further, an embodiment wherein a cooler that uses chemical energy can be attached to or detached from the eye pillow body as needed.

The eye pillow of the present invention uses chemical energy in its steam-generating unit and therefore, it can provide steam to the eyes and the area around the eyes at any time and easily when compared to providing steam to the eyes and the area around the eyes using a steam towel. Moreover, the steam temperature that is released from the surface of application to the eyes and the area around the eyes is kept at 50° C. or lower and therefore, it can be used comfortably and safely.

Moreover, total weight of the eye pillow of the present invention is 50 g or more and therefore, it can apply the appropriate pressure to the eyes and the area around the eyes. This pressure and providing steam have a synergistic, relaxing effect to induce a pleasant sleep.

Furthermore, by means of the embodiment with which the steam-generating unit or cooler that uses chemical energy can be attached to or detached from the eye pillow body as needed, one or both of the cooler and steam-generating unit can be attached to provide cold or warm steam, or both, while applying the appropriate pressure to the eyes and the area around the eyes in accordance with the eyestrain properties, preferences, sensation of effects, place of use, etc., of the person using the eye pillow. Consequently, by means of the eye pillow of this embodiment, it is possible to obtain a sensation of effects without restricting the properties, preferences, and place of use.

Moreover, when an aromatic component is used in the eye pillow of the present invention so that the eye pillow is fragrant therewith during application, the effects of the present invention can be enhanced even further.

BRIEF DESCRIPTION OF THE DRAWINGS

FIG. 6A is a plane view of an eye pillow of one embodiment of the present invention.

FIG. 6B is a cross section of the eye pillow in FIG. 6A.

DESCRIPTION OF THE PREFERRED EMBODIMENTS

Figure 1A:
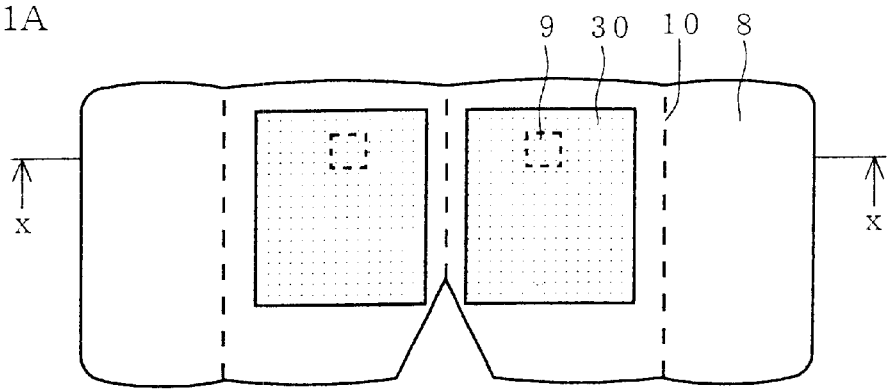
FIG. 1A is a plane view of an eye pillow of one embodiment of the present invention.

The eye pillow of the present invention is applied to the eyes and the area around the eyes. Application to the eyes and the area around the eyes here means the act of directly applying the eye pillow to the eyes and skin around the eyes to cover the eyes and the area around the eyes so that the eye pillow can apply pressure to the eyes and the area around the eyes.

One feature of the eye pillow of the present invention is that it has a steam-generating unit that uses chemical energy as the steam-generating source.

Chemical energy here can be the heat of neutralization between an acid and alkali, the heat of hydration of an inorganic salt (calcium chloride, magnesium chloride, calcium oxide, magnesium oxide, zeolite, etc.), the heat of oxidation of metal powder, etc.

The specific mode of using this chemical energy in the steam-generating unit is determined as needed in accordance with the reaction type of this chemical energy that is used. For instance, when the heat of neutralization between an acid and alkali or the heat of hydration of an inorganic salt, etc., is used, the steam-generating unit can comprise a heating part that generates the heat of neutralization and the heat of hydration or a vaporizing part with which steam is released by the heat generated from these reactions. In this case, the heating part should be constituted such that one reactant and the other reactant that react to each other are separated by a partition, and upon generating the steam, the reaction is allowed to proceed by breaking down the partition. Moreover, the vaporizing part should comprise a fiber aggregate or porous unit, such as paper, woven fabric, nonwoven fabric, etc., impregnated with water so that it releases steam when heat is generated by the heating part.

When the heat of oxidation of a metal powder is used as the chemical energy, the steam-generating unit comprises a steam-generating composition containing a metal powder (such as iron, aluminum, zinc, copper, etc.), a salt that serves as the catalyst (such as a chloride of an alkali metal, for instance, sodium chloride, potassium chloride, etc., or a chloride of an alkali earth metal, such as calcium chloride, magnesium chloride, etc.), and water. When necessary, this composition can contain a water-retaining agent (such as vermiculite, calcium silicate, silica gel, silica porous substance, alumina, pulp, wood flour, water-absorbing polymer, etc.), reaction accelerator (such as activated carbon, carbon black, graphite, etc.), etc. This steam-generating composition acts as a steam-generating unit by inducing an exothermic reaction whereby the metal powder is oxidized as shown by the following formula:

$$Fe+3/4O_2+3/2H_2O \rightarrow Fe(OH)_3+96kcal$$

to release the water within the system as steam.

Furthermore, the exothermic reaction of this steam-generating composition is used by a heat-generating unit generally referred to as a chemical heater. However, this composition is held in a bag made from a material with both low gas permeability and moisture permeability in conventional chemical heaters and is used so that water needed for the reaction will not escape from the heat-generating unit.

In contrast to this, when this composition is used as the steam-generating source of the present invention, this composition is held with a sheet material that preferably has a moisture permeability by ASTM methods (method E-96-80D) of 600 g/m²·24 hr or higher, more preferably, 1000 g/m²·24 hr or higher, particularly 1,500 to 3,200 g/m²·24 hr, so that some of the water present within the reaction system is actively released to the outside of the system as steam with the generation of heat. Thus, the amount of steam that is released can be 10 to 3,000 mg in 1 minute, depending on the components of this steam-generating composition and the material used for the bag that holds the steam-generating composition, and the amount of steam released per unit surface area of the surface of application of the eye pillow to the eyes and the area around the eyes can be 0.5 mg/cm²·min or more. Consequently, sufficient steam can be provided to the eyes and the area around the eyes.

The temperature of the steam that is released during the exothermic reaction of the steam-generating composition becomes 60° C. or higher when it is released or substantially released into the atmosphere without restricting the amount of air flowing into this composition. There is a possibility that steam at 60° C. or higher will pose problems in terms of safety when it is continuously applied to the eyes and the area around the eyes. Therefore, in the present invention, the temperature of the steam that is released from the surface of application of the eye pillow to the eyes and the area around the eyes is kept at 50° C. or lower, preferably 38 to 44° C.

This type of temperature control is also carried out when chemical energy from the above-mentioned heat of neutralization of an acid and alkali, heat of hydration of an inorganic salt, etc., is used in the present invention.

In order to keep the temperature of the steam that is released from the eye pillow at 50° C. or lower, this temperature is determined in accordance with the method of determining the temperature of disposable heaters of JIS S4100.

The specific embodiment of temperature control can be determined as needed in accordance with the reaction type of chemical energy used by the steam-generating unit, convenience, etc. For instance, it is possible to adjust the reaction speed by adjusting the amount of reactants to be reacted in the steam-generating unit, the particle diameter when a reactant is a powder, etc., as needed and thereby control the amount of steam that is released from the surface of the eye pillow. Moreover, it is also possible to place a temperature-regulating member between the steam-generating unit and the surface of the eye pillow to be applied to the eyes and the area around the eyes so that the steam that is released from the steam-generating unit passes through the temperature-regulating member and the steam temperature is thereby lowered. This type of temperature control with a temperature-regulating member is preferred because it is possible to reliably and easily keep the temperature of the steam released from the surface of the eye pillow at 50° C. or lower, regardless of the type of chemical energy that is used by the steam-generating unit.

At least one of (1) woven or nonwoven fabric, (2) papers, such as paper or synthetic paper, etc., (3) porous films or porous sheets formed from plastic, natural rubber, reclaimed rubber, or synthetic rubber, (4) foamed plastics, such as urethane foam with perforations, etc., and (5) metal foil, such as aluminum foil with micropores, etc., can be used as the constituent material of the temperature-regulating member.

Furthermore, when temperature is controlled using a temperature-regulating member made of these constituent materials, the temperature-regulating member will also be resistant to penetration by steam and therefore, thickness of the temperature-regulating member, etc., is determined as needed in accordance with the material used for this temperature-regulating member and, when several constituent materials are layered as the temperature-regulating member, how they are combined, etc., so that the desired amount of steam will reach the eyes and the area around the eyes. For instance, this thickness is preferably 0.1 mm or thicker, more preferably 1 mm or thicker, when the temperature-regulating material is formed from a single layer of nonwoven.

In addition, when the temperature-regulating material is formed from the above-mentioned constituent materials, it is preferred that the temperature-regulating material be a layered product made from multiple types of constituent materials in order to make thickness compact and to enhance its ability to regulate the steam that passes through this member.

In view of the effects of providing steam to the eyes and the area around the eyes, the amount of steam generated per unit surface area at the surface of the eye pillow applied to the eyes and the area around the eyes is preferably adjusted to be 0.01 mg/cm$^2$·min or more, and more preferably to be 0.5 mg/cm$^2$·min. These amounts of generated steam were calculated by the following formula:

Amount of steam generated (mg/cm$^2$·min)=(Wt$_0$−Wt$_{15}$)·1000/15S in which, when eye pillow is taken out from the container protecting it from outside air in a room-temperature environment (25° C., 65% RH) and placed immediately on a top-pan scale capable of measuring up to 3 places to the right of the decimal point and weight is determined for 15 minutes from that time on, Wt$_0$ (g) represents the weight of the eye pillow when the measurements were started, Wt$_{15}$ (g) represents the weight 15 minutes later and S (cm$^2$) represents the surface area of the surface of the eye pillow applied to the eyes and the area around the eyes.

As an example of a specific method for adjusting the amount of steam released from the surface of the eye pillow applied to the eyes and the area around the eyes to 0.01 mg/cm$^2$·min or more, a material with sufficient moisture permeability may be used for the bag holding the steam-generating composition, the temperature-regulating member, or the eye pillow body that determines the external shape, etc., when, for example, the steam-generating unit is made from the same steam-generating composition as in chemical heaters. More specifically, a material with moisture permeability by ASTM methods (method E-96-80D) of 600 g/m$^2$·24 hr or higher, preferably 1,000 g/m$^2$·hr or more, particularly 1,500 to 3,200 g/m$^2$·24 hr, is used. Woven or nonwoven fabric, paper, and synthetic paper made from one or a mixture of 2 or more selected from artificial fibers, such as nylon, vinylon, polyester, rayon, acetate, acrylic, polyethylene, polypropylene, polyvinyl chloride, etc., and non-permeable film or sheets with micropores made from polyethylene, polypropylene, polyamide, polyester, polyvinyl chloride, polyvinylidene chloride, polyurethane, polystyrene, ethyl-vinyl acetate copolymer saponification product, ethylene-vinyl acetate copolymer, natural rubber, reclaimed rubber, synthetic rubber, etc., are examples of this type of moisture-permeable material.

On the other hand, (1) nonwoven fabric, woven fabric and quilting made from cotton, silk, flax, synthetic fibers, etc., (2) papers, such as paper, synthetic paper, etc., and (3) animal hair, etc., can be used as the constituent material for the eye pillow body. Moreover, (1) organic polymer compounds such as polyethylene, polypropylene, polyester, etc., (2) ceramics such as silica, alumina, etc., (3) seeds, such as flaxseed, husks, such as Bruckwheat chaff, etc., (4) woven fabric and nonwoven fabric, (5) paper, wood, etc., can be used as a weight-adjusting material in order to obtain the total weight of 50 g or more.

There are no special restrictions to the shape of the eye pillow body, but in order to prevent the eye pillow from slipping off when it is applied to the eyes and the area around the eyes, it is preferred that, for instance, it have a sheet where a V-shaped cut is formed in the part that touches the nose or an eye mask-like shape. Moreover, it can be thin or thick to a certain extent, but in order to make the surface of the eye pillow fit the eyes and the area around the eyes when the eye pillow is applied, it is preferred that the surface of the eye pillow have irregularities that match the facial three-dimensional shape of the eyes and the area around the eyes so that the warm steam from the entire surface of the eye pillow that is applied, or the cold sensation from the cooler, which is discussed later, can actually be felt. This can be done by making specific irregularities by quilting when woven fabric, etc., is used as the constituent material of the eye pillow surface.

Moreover, the steam-generating unit in the shape of a small bag, etc., can be kept in or taken out from a pocket made in the surface of the eye pillow body as needed. A hook-and-loop fastener, a button, a hook, etc., can be used as securing means for stable securing of the steam-generating unit to the surface of the eye pillow body so that it can be inserted or taken out as needed or for preventing the steam generating held in the pocket from falling out.

When the steam-generating unit can be attached to or detached from the eye pillow body as needed, it is preferred that the cooler that uses chemical energy also be attached to or detached from the eye pillow body as needed.

With respect to the cooling properties of the cooler, it is preferred that the skin temperature around the eyes can be cooled in one minute after starting to cool by applying the cooler to the eyes and the area around the eyes, to 15° C. or higher and yet at least 5° C. lower than the temperature before the cooling is started, and that skin temperature around the eyes can be kept within this temperature range for 300 seconds or longer. By bringing the skin temperature around the eyes to 15° C. or higher after applying the cooler, the eyes and area around the eyes can be cooled comfortably and safely without excessive irritation of the skin. Moreover, because it is possible to cool to a temperature that is at least 5° C. lower than the temperature before cooling in 1 minute after starting cooling and retain this temperature for 300 seconds or longer, the sensation of the effects of cooling can be realized sufficiently.

An endothermic reaction by mixing with water, etc., can be given as an example of the chemical energy used by the cooler. Urea and inorganic ammonium salts, such as ammonium nitrate, ammonium sulfate, ammonium phosphate, diammonium hydrogenphosphate, ammonium metavanadate, ammonium chloride, ammonium bromide, ammonium iodide, etc., are examples of cold medium components that induce this type of endothermic reaction.

It is preferred that these cold medium components and water be sealed separately in different bags during storage of the cold unit or before the cold unit is attached to the eye pillow body so that they can be mixed when necessary.

Various additives can be combined as needed with the reaction system of the cold medium component and water. For instance, when a certain viscosity is needed, it is possible to add 1 to 5 parts by weight of a gum, such as xanthan gum or guar gum, etc., water-absorbing polymer, etc., as the gelling agent per 100 parts by weight cold medium components when the cold medium components and water are mixed. Moreover, it is preferred that the composition be 67 to 200 parts by weight water and 1 to 5 parts by weight gum per 100 parts by weight cold medium components in order to realize the above-mentioned cooling properties with this system.

There are no special restrictions to the constituent material used for the bags in which the cold medium components, water, etc., are sealed. Examples are single-layer or multi-layer film of synthetic resin film, such as polyethylene, polypropylene, polyamide, etc., these films laminated with metal foil or metal-evaporated film, etc.

The structure of the bag in which the cold medium components and water, etc., are sealed can be, for instance (i) a two-layer structure where an inner bag is placed in an outer bag or (ii) structure where a partition is placed inside a bag so that the inside is divided into 2 or more chambers, so that these can be sealed separately during storage or before use of the cooler and mixed when needed.

Of these, a specific example of the two-layer structure in (i) is to fill water inside the inner bag and seal the cold medium components between the inner bag and outer bag, or fill the cold medium components inside the inner bag and seal the water between the inner bag and outer bag. In this case, the inner bag is made so that it will not easily break under normal storage conditions but will break when outside pressure is applied when the cooler is used. In order to do this, the film material comprising the inner bag is relatively weak in comparison to the film material comprising the outer bag, or the strength of the seal of the inner bag is relatively weak when compared to the seal of the outer bag.

A specific example of the structure in (ii) is to seal the cold medium component in one of the 2 adjacent chambers separated by the partition and fill water in the other. In this case, the shape and strength of the partition should be such that the two chambers that are separated become continuous when outside force is applied when the cooler is used.

The overall shape of the cooler should be flexible and flat in a natural state. Moreover, it can also have an eye mask-type shape so that it fits the eyes and the area around the eyes. In addition, there can be a cover member on the outside of the cooler.

A woven or nonwoven fabric, etc., of natural fibers or synthetic fibers is preferred as the cover member. It is preferred that basis weight of the same be 10 $g/m^2$ to 500 $g/m^2$, particularly 20 $g/m^2$ to 30 $g/m^2$, and that thickness of the fiber layer when a weight of 4 $g/m^2$ is applied is 0.05 mm to 1.00 mm, particularly 0.10 mm to 0.50 mm. Thus, a clammy sensation due to dew condensation can be prevented and a soft feeling will be given. Moreover, it will be possible to prevent smudging of cosmetics that have been applied to the face. Furthermore, it is possible to improve the ease with which the cooler is attached to and detached from the eye pillow body by covering the cooler with a cover member made from the above-mentioned woven or nonwoven fabric when the male member of a hook-and-loop fastener is placed on the eye pillow body in order in order to attach or detach the cooler from the eye pillow body as needed.

The total weight of the eye pillow should be 50 g or more, preferably 80 g or more, in order to apply the appropriate pressure to the eyes and the area around the eyes when the eye pillow is placed on the eyes and the area around the eyes and thereby induce a relaxed and refreshed feeling. Moreover, if total weight of the eye pillow is too heavy, there will be too much resistance for the steam that is released from the steam-generating unit to pass through to the surface of application of the eye pillow to the eyes and the area around the eyes and therefore, it is preferred that total weight of the eye pillow be 400 g or less, particularly 250 g or less.

An aromatic component is preferably added to the eye pillow to give off an aroma when the eye pillow is used. The aromatic component is one that induces a relaxed and refreshed feeling and a pleasant sleep and preferably an herb, such as lavender, mint, rose, etc. There are no special restrictions to the method of providing the aromatic component and the method whereby aromatic component carrier, such as inorganic particles of silica, cellulose, etc., organic particles of cellulose, ethylene vinyl acetate copolymer, etc., impregnated with the aromatic compound that becomes the aromatic component, or potpourri, such as real lavender, etc., is mixed in the weight-adjusting material of the eye pillow, the method whereby fragrant oil is applied to the surface material of the eye pillow or the eye pillow body when the eye pill is used, the method of attaching a fragrant sheet to the eye pillow, the method of inserting a fragrant bag inside the eye pillow, etc., can be given as examples.

Preferred embodiments of the present invention will be described in detail below while referring to the drawings. Furthermore, the same or equivalent constituent elements are represented by the same number in each figure.

Figure 4A:
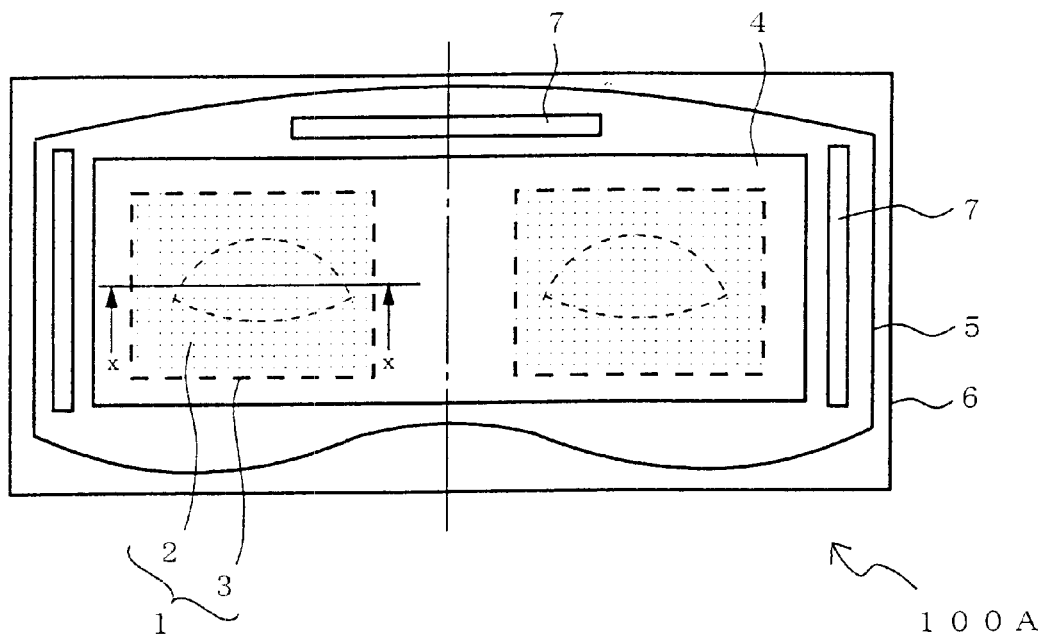
FIG. 4A is a plane view of an eye pillow of one embodiment of the present invention.
Figure 4B:
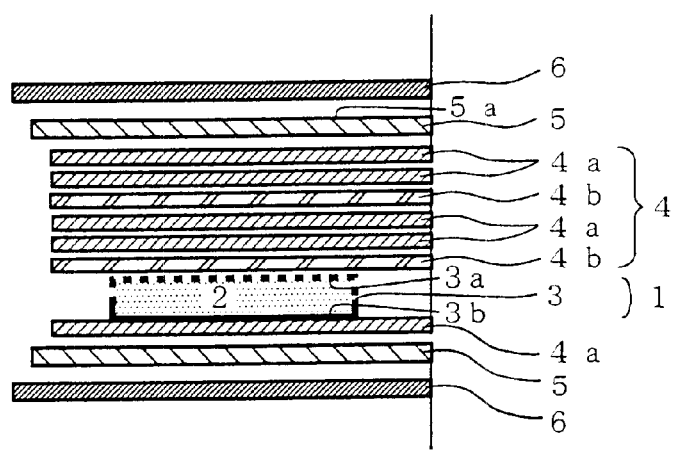
FIG. 4B is a cross section of the eye pillow in FIG. 4A.

FIG. 4A is a plane view of eye pillow 100A of the first embodiment of the present invention and FIG. 4B is a partial cross section of the same. The broken line in the figures shows the position of the eyes when the eye pillow is applied to the eyes and the area around the eyes.

This eye pillow 100A comprises steam-generating unit 1 in which steam-generating composition 2 is held in moisture-permeable inner bag 3, temperature-regulating member 4 layered on steam-generating unit 1, moisture-permeable outer bag 5 in which all of these are held, and sealed bag 6 in which these are sealed around the outside.

This eye pillow 100A is sealed in sealed bag 6 during storage when not in use. This sealed bag 6 is broken during use and eye pillow 100A is taken out. Moreover, steam-generating surface 5a of moisture-permeable outer bag 5 is used by application to the eyes and the area around the eyes.

Steam-generating surface 1 is placed inside 2 different parts of eye pillow 100A so that it will cover both eyes and around the same when eye pillow 100A has been applied to the eyes and the area around the eyes.

Steam-generating composition 2 uses the above-mentioned heat of oxidation.

The surface on the side of moisture-permeable inner bag 3 that is applied to the eyes (steam-generating surface 3a) is made from a moisture-permeable material, while surface 3b on the other side is made from a moisture non-permeable material. This, by making one surface 3b of the moisture-permeable inner bag 3 holding steam-generating composition 2 moisture non-permeable, steam that has been released from steam-generating composition 2 can be effectively introduced to the eyes and the area around the eyes.

There are no special restrictions to the moisture-permeable material comprising steam-generating surface 3a as long as the amount of steam that passes through is sufficient and steam-generating composition 2 does not leak. Specific examples are woven or nonwoven fabric, paper, and synthetic paper made from one or a mixture of 2 or more selected from artificial fibers, such as nylon, vinylon, polyester, rayon, acetate, acrylic, polyethylene, polypropylene, polyvinyl chloride, etc., and non-permeable film or sheets with micropores made from polyethylene, polypropylene, polyamide, polyester, polyvinyl chloride, polyvinylidene chloride, polyurethane, polystyrene, ethylvinyl acetate copolymer saponification product, ethylenevinyl acetate copolymer, natural rubber, reclaimed rubber, synthetic rubber, etc.

Moisture non-permeable surface 3b of moisture-permeable inner bag 3 is attached and secured to nonwoven fabric 4 a as the securing base.

The temperature-regulating member 4 laminated on steam-generating surface 3a of moisture-permeable inner bag 3 is made from a laminate of 4 pieces of nonwoven fabric 4a and 2 pieces of paper 4b, as shown in FIG. 4B. Furthermore, temperature-regulating member 4 of the present invention is not limited to the embodiment of this eye pillow 100A in FIGS. 4A and 4B and a variety of the above-mentioned constituent materials can be used alone or in combination with one another. Moreover, moisture-permeable inner bag 3 can be given the function of temperature-regulating member 4 without separately placing temperature-regulating member 4 inside moisture-permeable inner bag 3 as eye pillow in FIGS. 4A and 4B. However, it is preferred that temperature-regulating member 4 is formed separately from moisture-permeable inner bag 3 in terms of economics, technology, production ease, safety, etc.

Moisture-permeable outer bag 5 houses all of moisture-permeable inner bag 3 holding steam-generating composition 2 and temperature-regulating member 4, and its external shape is an eye mask-type shape. The fit of eye pillow 100A will feel better when moisture-permeable outer bag 5 with this type of external shape when eye pillow 100A is applied is an eye mask-type shape. Furthermore, the eye mask shape can be thick to a certain extent or it can be a thin-sheet shape.

Adhesive material 7 is placed around the outside of the surface of moisture-permeable outer bag 5 applied to the eyes and the area around the eyes (steam-generating surface 5a). Thus, it is possible to easily secure eye pillow 100A to the eyes and the area around the eyes. Furthermore, eye pillow 100A can be secured to any place by being supported by the hands and therefore, adhesive material 7 is optional in the present invention.

Figure 1B:
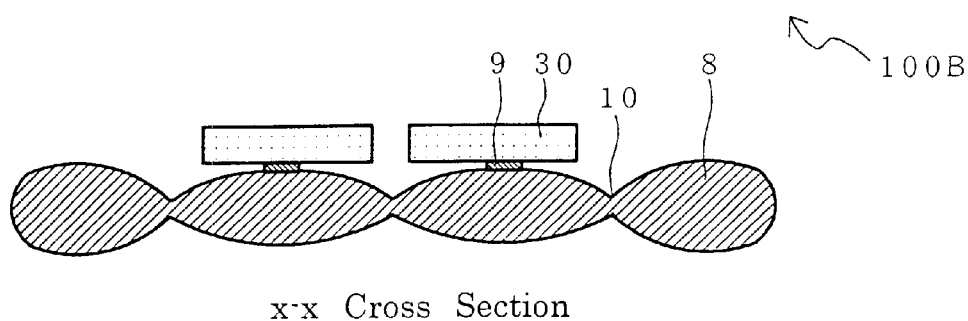
FIG. 1B is a cross section of the eye pillow in FIG. 1A.

FIG. 1A is a plane view of eye pillow 100B of the present invention that is different from FIGS. 4A and 4B and FIG. 1B is a cross section of the same. This eye pillow 100B is made from 1 piece of sheet-shaped eye pillow body 8 and steam generator 30, which is fastened to one surface of eye pillow body 8 (surface on the side opposite the surface that is applied to the skin) with hook-and-loop fastener 9 so that it can be attached and detached as needed.

Steam generator 30 is steam-generating unit 1 formed as in FIG. 4A and FIG. 4B, or steam-generating unit 1 with temperature-adjusting member 4. A piece of hook-and-loop fastener is placed on the side of steam-generating unit 30 opposite the surface applied to the skin.

The surface of eye pillow body 8 is a woven or nonwoven fabric made from cotton, silk, flax, synthetic fibers, etc., and quilting material to which 80 to 150 g polyethylene particles with a diameter of 2 to 7 mm have been added is formed as the weight-adjusting material on the inside. Moreover, 0.1 to 10 g aromatic component carrier impregnated with real lavender, dry herbs, essential oils, etc., are added to the inside of the quilting material of eye pillow body 8. Moreover, it is also possible to give the material inside the quilting the function of the temperature-regulating member.

The external shape of eye pillow body 8 is almost rectangular at 20 cm×8 cm and large enough so that it covers both eyes and around the same. A V-shaped cut is formed into the center on one side. Moreover, quilting seams 10 are made in the surface of steam generator 30 fastened to eye pillow body 8 to match the position of the rim of steam generator 30 that is fastened and this same part can be easily folded. By making seams 10 in this way, it is possible to prevent the contents, such as weight-adjusting material, etc., from moving to one side and improve even further fit when eye pillow body 8 is applied to the eyes and the area around the eyes.

Figure 2A:
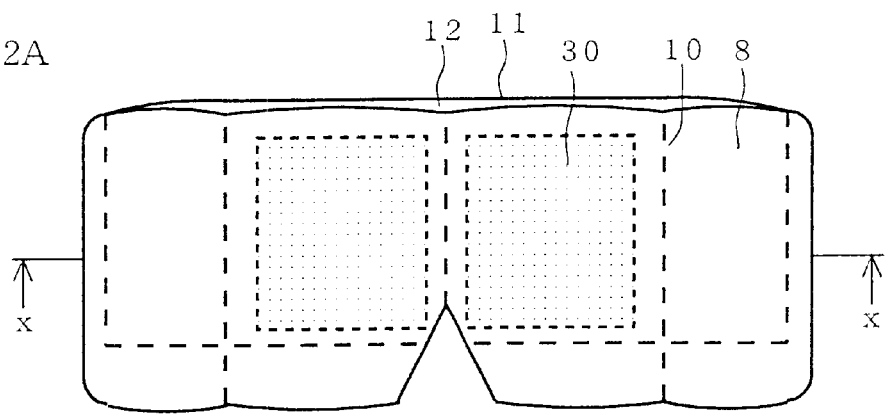
FIG. 2A is a plane view of an eye pillow of one embodiment of the present invention.
Figure 2B:
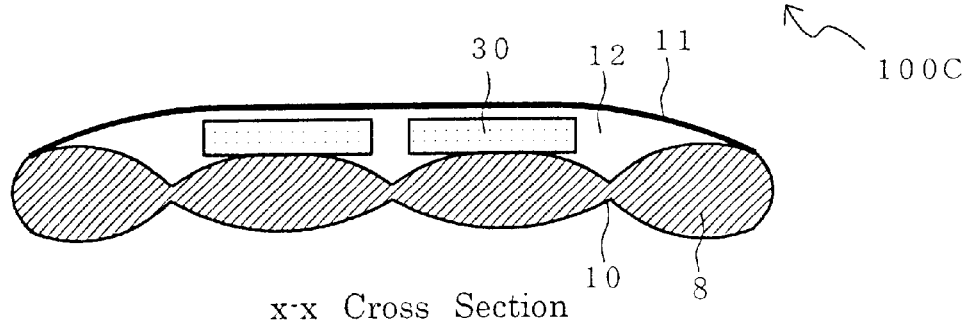
FIG. 2B is a cross section of the eye pillow in FIG. 2A.

It is preferred that eye pillow 100C. in FIGS. 2A and 2B is made from the same quilting material as eye pillow 8 in FIGS. 1A and 1B. Cloth 11 made from woven or nonwoven fabric of cotton, silk, flax, synthetic fibers, etc., is further applied on the outside of this to form pocket 12 that holds steam generator 30. It is preferred that a button, tape, hook, zipper, etc., be placed in the opening of pocket 12 of this eye pillow body 8 so that steam generator 30 held inside pocket 12 will not needlessly slip out.

Figure 3A:
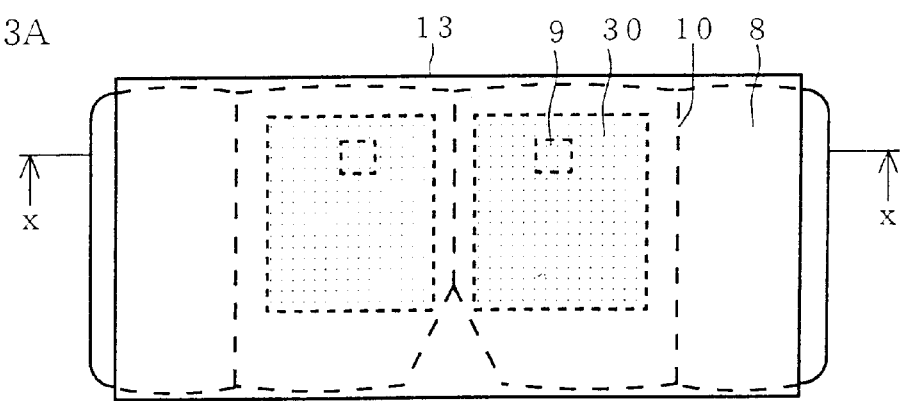
FIG. 3A is a plane view of an eye pillow of one embodiment of the present invention.
Figure 3B:
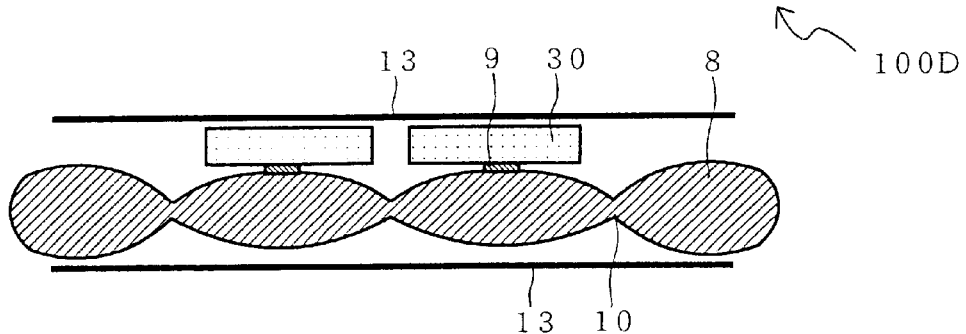
FIG. 3B is a partial cross section of the eye pillow in FIG. 3A.

Eye pillow 100D of FIGS. 3A and 3B is eye pillow 100B in FIGS. 1A and 1B covered with cover 13 made of nonwoven fabric, woven fabric, etc.

Figure 5A:
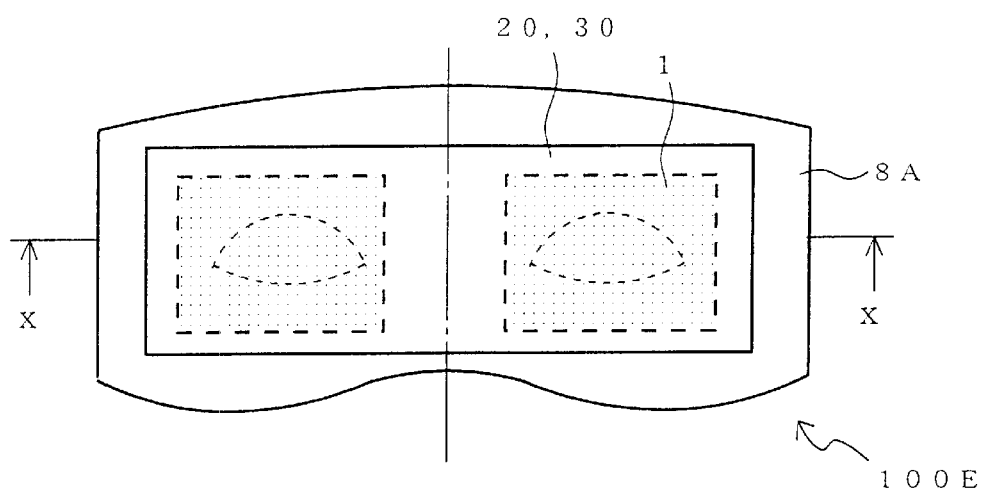
FIG. 5A is a plane view of an eye pillow of the present invention with a cooler or steam-generating unit attached.
Figure 5B:
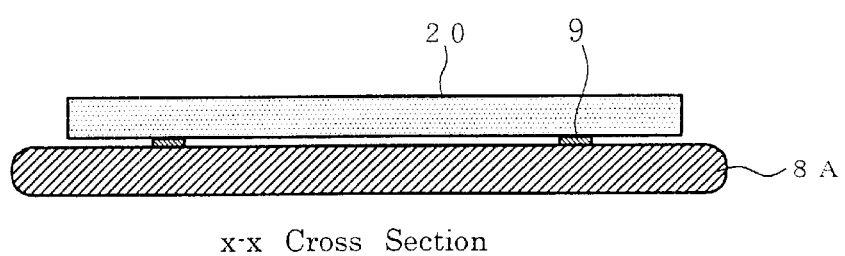
FIG. 5B is a cross section of the eye pillow in FIG. 5A with a cooler attached.

FIG. 5A is the plane view of eye pillow 100E of the present invention with cooler 20 or steam generator 30. FIG. 5B is a cross section of eye pillow 100E with cooler 20 and FIG. 5C. is a cross section of eye pillow 100E with steam generator 30. The dotted lines in FIG. 5A show the position of the eyes when eye pillow 100E is applied to the eyes and the area around the eyes.

As with eye pillow body 8 of eye pillow 100B in FIGS. 1A and 1B, the external shape of this eye pillow body 8 A is large enough the cover both eyes and around the same and is, for instance, an eye mask-like shape of 8 cm (length)×20 cm (width)×1 cm (thickness). The surface of eye pillow body 8 A is made from a woven or nonwoven fabric of cotton, silk, flax, synthetic fibers, etc. and the inside is filled with 80 to 150 g polyethylene particles with a diameter of 2 to 7 mm as the weight-adjusting material and 0.1 to 10 g aromatic component carrier impregnated with as real lavender, dry herbs, essential oil, etc.

Hook-and-loop fastener 9 is placed on the surface of eye pillow body 8 A so that cooler 20 and steam generator 30 can be attached and detached as needed.

Steam generator 30 has the same structure as the layered unit of steam-generating unit 1, temperature-regulating member 4, and moisture-permeable outer bag 5 shown in FIG. 4B, and the entire steam generator 30 is sealed in a sealed bag before being attached to eye pillow body 8A.

Figure 5C:
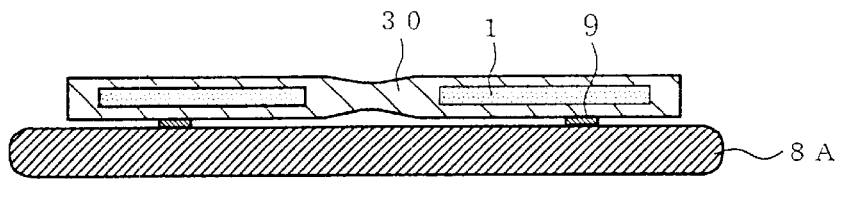
FIG. 5C is a cross section of the eye pillow in FIG. 5A with a steam-generating unit attached.

As shown in FIG. 5C, steam generator 30 covers both eyes and around the same when it is attached to eye pillow body 8 A and applied to the eyes and the area around the eyes. However, steam-generating unit 1 is placed in 2 places inside steam generator 30.

Cooling and warming eye pillow 100F in FIGS. 6A and 6B is such that pockets 12A and 12B are made with cloth 11 on both sides of eye pillow body 8 and cooler 20 is placed in one pocket 12A, while steam generator 30 is placed in the other pocket 12B The eye pillow of the present invention can take on a variety of embodiments. For instance, in order to introduce steam that is released from steam-generating unit 1 efficiently to the eyes and the area around the eyes, eye pillow 100A shown in FIGS. 4A and 4B can have surface 3b that is moisture non-permeable on the side opposite the eye of moisture-permeable inner bag, or the entire surface of moisture-permeable inner bag 3 can be made from a moisture-permeable material and a moisture non-permeable sheet can be placed on top of surface 3b on the side opposite the surface of this moisture-permeable inner bag 3 that is applied to the eyes and the area around the eyes. In addition, it is also possible to use one steam-generating unit big enough to cover both eyes and around the same when the eye pillow is applied as steam-generating unit 1.

EXAMPLES

Example 1

Eye pillow 100B of the embodiment in FIGS. 1A and 1B was made as follows:

First, 40 parts by weight 2 wt % brine were added to 10 parts by weight water-absorbing polymer (Mitsubishi Kagaku; brand name Aquapearl) to make the water-containing water-retaining agent.

On the other hand, 50 parts by weight of the above-mentioned water-containing water-retaining agent were added to a mixture of 30 parts by weight iron powder with a particle diameter of 32 $\mu$m or smaller (Dowa Tetsufun Co., Ltd., brand name RKH), 10 parts by weight activated carbon (Takeda Yakuhin Co., Ltd.), and 10 parts by weight vermiculite (Shinsei Mickuron Co., Ltd., vermiculite) to obtain steam generating composition 2 (see FIG. 4B). This steam-generating composition 2 was filled into a small bag (3 cm×3 cm square), one surface of which was made from a vinyl-coated sheet (Nitto Denko Co., ltd., brand name: Nitotack) and the other surface of which was made from moisture-permeable nonwoven fabric (Mitsui Kagaku Co., Ltd.; brand name Syntex MB, basis weight of 15 g/m$^2$) to obtain steam-generating unit 1.

This steam-generating unit 1 was secured by adhesion to nonwoven fabric (Chisso Co., Ltd.; brand name Airade, basis weight of 24 g/m$^2$) with the surface made from moisture-permeable nonwoven fabric facing up and the bottom surface serving as the substrate. The same temperature-regulating member as temperature-regulating member 4 in FIG. 4B (1 layer of paper 4b (Kureshia Co., Ltd.; brand name Kimutowel), 2 layers of nonwoven fabric 4a (Chisso Co., Ltd.; brand name Airade, basis weight of 24 g/m$^2$, 1 layer of paper 4b, and 2 layers of nonwoven fabric 4a layered in succession) was placed on the top of this steam-generating unit 1 and the entire product was held in outer bag 5 made from moisture-permeable nonwoven fabric (Mitsui Kagaku co., Ltd; brand name: Syntex MB, basis weight 15 g/m$^2$) to make steam generator 30 with a temperature-adjusting member. This steam-generator 30 was stored in a sealed bag.

Next, eye pillow body 8 (20 cm×8 cm) was made from quilting material whose surface material was cotton cloth and inside which was filled 100 g polyethylene particles with a diameter of 5 mm as the weight-adjusting material and 1 g real lavender and a V-shaped cut was formed in the center of one side. Straight quilting seams 10 were made in the center of one side of this eye pillow body 8 and at the left and right positions of 6 cm away from the center. Moreover, hook-and-loop fastener 9 (2 cm×2 cm square) was placed in the center and at the left and right positions of 3 cm away from the center.

Steam generator 30 with the temperature-regulating member was taken out from the sealed bag and glued directly on hook-and-loop fastener 9 on eye pillow body 8 to obtain eye pillow 100B. This eye pillow 100B was applied to the eyes and the area around the eyes looking up with steam generator 30 facing the skin side.

Eye pillow 100B started to generate steam approximately 30 to 40 seconds after taking out steam generator 30 from the sealed bag. The maximum temperature of the steam released from the surface of eye pillow 100B applied to the eyes and the area around the eyes was 40 to 41° C. Moreover, this eye pillow 100B continued to generate steam at 38° C. or higher for 15 minutes.

The results after application of eye pillow 100B were evaluated by a 10-member expert panel for the following evaluation items based on criteria in 5 steps. Table 1 shows the average of evaluation values of the 10-member expert panel:

Overall Effect
5: Effective
4: Somewhat effective
3: Cannot say either way
2: Almost no effect
1: No effect
Recovery from Eye Fatigue
5: Effective
4: Somewhat effective
3: Cannot say either way
2: Almost no effect
1: No Effect
Relaxing, refreshing
5: Effective
4: Somewhat effective
3: Cannot say either way
2: Almost no effect
1: No effect
Pleasant Sleep
5: Effective
4: Somewhat effective
3: Cannot say either way
2: Almost no effect
1: No effect
Fit
5: Effective
4: Somewhat effective
3: Cannot say either way
2: Almost no effect
1: No effect Example 2

Eye pillow 100C of the embodiment in FIGS. 2A and 2B was made. In this case, eye pillow body 8 was made from the same quilting material as in Example 1 and pocket 12 that holds steam-generator 30 was made on one side.

Steam generator 30 with a temperature-regulating member of Example 1 was taken out from the sealed bag and placed directly inside pocket 12 of eye pillow body 8 to obtain eye pillow 100C. This eye pillow 100C. was applied to the eyes and the area around the eyes looking up so that the pocket 12 side of the eye pillow body 8 touched the skin.

Eye pillow 100C. started generating steam approximately 30 to 40 seconds after taking out steam generator 30 from the sealed bag. The maximum temperature of the steam that was released from the surface of eye pillow 100C. that was applied to the eyes and the area around the eyes was 39 to 40° C. Moreover, this eye pillow 100C. continued to generate steam at 38° C. or higher for 15 minutes.

The effects after application of eye pillow 100C. were evaluated as in Example 1. The results are shown in Table 1.

Example 3

An eye pillow was made and applied to the eyes and the area around the eyes as in Example 1, with the exception that the amount of weight-adjusting material (polyethylene particles with a diameter of 5 mm) in the production of eye pillow 100B was changed to 50 g.

As a result, the eye pillow started generating steam approximately 30 to 40 seconds after taking out steam generator 30 from the sealed bag. The maximum temperature of the steam that was released from the surface of the eye pillow that was applied to the eyes and the area around the eyes was 40 to 41° C. Moreover, this eye pillow continued to generate steam at 38° C. or higher for 15 minutes.

The effects after application of the eye pillow were evaluated as in Example 1. The results are shown in Table 1.

Example 4

An eye pillow was made and applied to the eyes and the area around the eyes as in Example 1, with the exception that real lavender was not added in the production of eye pillow 100B.

As a result, the eye pillow started generating steam approximately 30 to 40 seconds after taking out steam generator 30 from the sealed bag 6. The maximum temperature of the steam that was released from the surface of steam generator 30 that was applied to the eyes and the area around the eyes was 40 to 41° C. Moreover, this steam generator continued to generate steam at 38° C. or higher for 15 minutes.

The effects after application of the eye pillow were evaluated as in Example 1. The results are shown in Table 1.

Comparative Example 1

Steam generator 30 with a temperature-regulating member of Example 1 was taken out from the sealed bag and directly applied to the eyes and the area around the eyes looking up.

As a result, this steam generator 30 started generating steam approximately 30 to 40 seconds after taking out steam-generating unit 1 from the sealed bag. The maximum temperature of the steam that was released from the surface of the eye pillow that was applied to the eyes and the area around the eyes was 40 to 41° C. Moreover, this eye pillow continued to generate steam at 38° C. or higher for 15 minutes.

The effects after application of steam generator 30 were evaluated as in Example 1. The results are shown in Table 1.

Comparative Example 2

An eye pillow was made and applied to the eyes and the area around the eyes as in Example 2, with the exception that the amount of weight-adjusting material (polyethylene particles with a diameter of 5 mm) in the production of eye pillow 100B was changed to 20 g.

As a result, the eye pillow started generating steam approximately 30 to 40 seconds after taking out steam generator 30 from the sealed bag 6. The maximum temperature of the steam that was released from the surface of the eye pillow 100B that was applied to the eyes and the area around the eyes was 40 to 41° C. Moreover, this eye pillow continued to generate steam at 38° C. or higher for 15 minutes.

The effects after application of the eye pillow were evaluated as in Example 1. The results are shown in Table 1.

Comparative Example 3

A commercial eye pillow without steam-generating capability (19 cm×100 cm rectangle weighing 159 g with lavender scent) was applied to the eyes and the area around the eyes looking up.

Moreover, the effects after application of the eye pillow were evaluated as in Example 1. The results are shown in Table 1.

TABLE 1

|  | Ex. | | | | Com. | | |
| --- | --- | --- | --- | --- | --- | --- | --- |
|  | 1 | 2 | 3 | 4 | 1 | 2 | 3 |
| Overall effect | 4.7 | 4.6 | 4.0 | 3.6 | 2.2 | 2.5 | 1.9 |
| Recovery from eye fatigue | 4.5 | 4.4 | 4.5 | 4.3 | 3.2 | 3.1 | 1.5 |
| Relaxing, refreshing | 4.7 | 4.6 | 4.0 | 1.5 | 1.5 | 2.5 | 3.4 |
| Pleasant sleep | 4.6 | 4.6 | 4.0 | 2.0 | 1.9 | 2.3 | 2.1 |
| Fit | 4.7 | 4.7 | 4.0 | 4.7 | 1.4 | 2.9 | 4.7 |

It is clear from the results in Table 1 that tired eyes are soothed to provide a relaxed and refreshed feeling and induce pleasant sleep by the eye pillows of the examples because steam is provided to the eyes and the area around the eyes and because the steam is applied [to the eyes and the area around the eyes under the appropriate pressure.

Example 5

(1) Production of eye pillow body

Eye pillow body 10F of the embodiment shown in FIGS. 6A and 6B was made.

In this case, eye pillow body 8 was made from the same quilting material as in Example 1 and pockets 12A and 12B were made on both sides using cotton cloth.

(2) Production of cooler

An outer bag (V-shaped cut in the center of one long side of a rectangle with inner dimensions of 160 mm×60 mm ×7 mm) and an inner bag (inner dimensions of 40 mm×50 mm ×5 mm) were made from polyethylene film (thickness of 60 μm). Twenty grams of water were sealed in the inner bag and cooling medium components consisting of 19.4 g ammonium nitrate, 0.3 g xanthan gum, and 0.3 g guar gum were sealed in between the outer bag and inner bag to obtain a cooler. In this case, one end of the inner bag had a weak seal strength. The part with the weak seal could be opened by hitting the inner bag from the outside of the outer bag at the time of use.

(3) Production of steam generator

The same steam generator 30 with a temperature-regulating member as in Example 1 was made.

(4) Evaluation

The cooler obtained in (2) was hit to open the inner bag and mix the water and cooling medium components and inserted into pocket 12A of the eye pillow body of (1). This eye pillow was applied for 10 minutes to the eyes and the area around the eyes of subjects (10 people) looking up. The tip of the temperature determination part of a thermocouple was pressed against the eyelids with cellophane tape and changes over time in skin surface temperature when the cooler was used were determined in an environment with a temperature and humidity of 20° C. and 60% RH. As a result, temperature was 25° C. after 2 minutes of cooling, 22° C. after 4 minutes, 22° C. after 6 minutes, 24° C. after 8 minutes, and 25° C. after 10 minutes.

Next, steam generator 30 that was obtained in (3) was taken out from the airtight bag and inserted in pocket 12B of the eye pillow body in (1). This eye pillow was applied for 15 minutes to the eyes and the area around the eyes of subjects looking up. This eye pillow started generating heat approximately 30 to 40 seconds after being applied to the eyes. The maximum temperature of this warm steam was 39 to 40° C. and warm steam at 38° C. or higher continued to be generated for approximately 15 minutes.

The evaluations of each subject when the cooler and steam generator were used on the eyes and the area around the eyes in succession were obtained for each of the following evaluation items and the average rating for each evaluation item was found. The results are shown in Table 2.

Overall Effect
5: Effective
4: Somewhat effective
3: Cannot say either way
2: Almost no effect
1: No effect
Recovery from Eye Fatigue
5: Effective
4: Somewhat effective
3: Cannot say either way
2: Almost no effect
1: No effect
Relaxing, Refreshing
5: Effective
4: Somewhat effective
3: Cannot say either way
2: Almost no effect
1: No effect
Pleasant Sleep
5: Effective
4: Somewhat effective
3: Cannot say either way
2: Almost no effect
1: No effect
Fit
5: Effective
4: Somewhat effective
3: Cannot say either way
2: Almost no effect
1: No effect Example 6
(1) Production of eye pillow body An eye pillow body was made by placing the male member of hook-and-loop fastener (2 cm×2 cm square) at the position of 4 cm away from the center to the left and right of the eye pillow body as in Example 1.

(2) Production of cooler

The entire outside surface of the cooler obtained in Example 5 (2) was covered with nonwoven fabric with a basis weight of 25 g/m² and a thickness of the fiber layer when a weight of 4 g/m² was applied of 0.25 mm.

(3) Production steam generator

A steam generator with a temperature-regulating member was made as in Example 1.

(4) Evaluations

The cooler obtained in (2) was hit to open the inner bag and mix the water and cooling medium components and inserted into pocket 12A of the eye pillow body of (1). This was applied to subjects and changes over time in skin surface temperature were determined as in evaluations of the cooler in Example 5 (4). As a result, it was 21° C. after 2 minutes of cooling, 19° C. after 4 minutes, 20 ° C. after 6 minutes, 21° C. after 8 minutes, and 22° C. after 10 minutes.

Next, the steam generator obtained in (3) of the present example was taken out from the air-tight bag and glued to the hook-and-loop fastener of the eye pillow body in (1) of the present example. This was applied to subjects and temperature of the warm steam that was generated was determined as in the evaluations of the steam generator in (4) of Example 1. As a result, the steam generator started generating steam approximately 30 to 40 seconds after being applied to the eyes. Maximum temperature of the warm steam was 40 to 41° C. and warm steam at 38° C. was continually generated for approximately 15 minutes.

Evaluations after application of the cooler and steam generator were performed as in Example 5. The results are shown in Table 2.

TABLE 2

|  | Ex. | |
| --- | --- | --- |
|  | 5 | 6 |
| Overall effect | 4.7 | 4.7 |
| Recovery from eye fatigue | 4.6 | 4.6 |
| Relaxing, refreshing | 4.7 | 4.7 |
| Pleasant sleep | 4.6 | 4.6 |
| Fit | 4.7 | 4.7 |

It is clear from the results in Table 2 that tired eyes are soothed to provide a relaxed and refreshed feeling and induce pleasant sleep by the eye pillows of the examples because cold air and steam are provided to the eyes and the area around the eyes and the appropriate pressure is applied to the eyes and the area around the eyes.

The entire disclosures of the claims, specifications and figures of Japanese Patent Application Nos. 11-287435, 11-371966 and 2000-269305 filed on Oct. 7, 1999, Dec. 27, 1999 and Sep. 5, 2000, respectively, are hereby incorporated by reference.

What is claimed is:

1. An eye pillow applied to the eyes and the area around the eyes, comprising a steam-generating unit that uses chemical energy, wherein steam at 50° C. or lower is released from the surface of the eye pillow applied to the eyes and the area around the eyes and the total weight of the eye pillow is 50 g or more.

2. The eye pillow according to claim 1, wherein the steam-generating unit is removably attached to the eye pillow body.

3. The eye pillow according to claim 2, wherein a cooler that uses chemical energy is removably attached to the eye pillow body.

4. The eye pillow according to claim 3, wherein means for securing the steam-generating unit or cooler is provided to the eye pillow body.

5. The eye pillow according to claim 3, wherein the cooler cools the skin around the eyes to no lower than 15° C. and yet at least 5° C. lower than before cooling, in one minute after beginning to cool the eyes and the area around the eyes, and keeps the temperature of the skin around the eyes in said temperature range for 300 seconds or more.

6. The eye pillow according to claim 1, wherein an aromatic component is added.

7. The eye pillow according to claim 2 or claim 3, wherein the eye pillow body has an eye mask-like shape that covers the eyes and the area around the eyes.

* * * * *